US007753851B2

(12) United States Patent
Nilsson

(10) Patent No.: US 7,753,851 B2
(45) Date of Patent: Jul. 13, 2010

(54) ROBOT FOR ULTRASONIC EXAMINATION

(75) Inventor: Dan Nilsson, Skelleftea (SE)

(73) Assignee: Mobile Robotics Sweden AB, Skelleftea (SE)

(*) Notice: Subject to any disclaimer, the term of this patent is extended or adjusted under 35 U.S.C. 154(b) by 552 days.

(21) Appl. No.: 11/786,873

(22) Filed: Apr. 13, 2007

(65) Prior Publication Data

US 2007/0205785 A1 Sep. 6, 2007

Related U.S. Application Data

(63) Continuation-in-part of application No. PCT/SE2004/001492, filed on Oct. 18, 2004.

(51) Int. Cl.
*A61B 8/14* (2006.01)
*G06F 17/00* (2006.01)

(52) U.S. Cl. .......................... 600/459; 700/245; 901/15

(58) Field of Classification Search ................. 600/407, 600/437, 459; 606/130; 700/245; 901/15
See application file for complete search history.

(56) References Cited

U.S. PATENT DOCUMENTS 4,014,207 A 3/1977 Meyer et al.
4,381,787 A 5/1983 Hottinger
4,444,197 A 4/1984 Koyano et al.
6,325,760 B1 12/2001 Takanori et al.
6,425,865 B1 7/2002 Salcudean et al.

FOREIGN PATENT DOCUMENTS

DE 3908648 9/1990
EP 0654244 5/1995
WO 9747441 12/1997
WO 2004016401 2/2004

OTHER PUBLICATIONS

File EPODOC/EPO, Aloka Co LTD: "Ultrasonic wave probe and ultrasonic diagnostic system", JP 80339623 A, 19960206 abstract.

*Primary Examiner*—Eric F Winakur
*Assistant Examiner*—Michael T Rozanski
(74) *Attorney, Agent, or Firm*—Mark P. Stone

(57) ABSTRACT

A robot for medical ultrasonic examination has an articulated robot arm with a plurality of arm units (14-16), mounted one on the other to be pivotable, and a computerized system for controlling the movements of the arm, the outermost arm unit being arranged to carry a probe. The outermost arm unit has a carrying member rotatable about a longitudinal axis (IV), and carries a probe holder pivotable about a transverse axis (V) perpendicular to the longitudinal axis (IV). The probe holder has a housing rotatable about the transverse axis, and a holder sleeve rotatable about a longitudinal axis (VI). The three axes (IV, V, VI) intersect at a single point. The probe holder has an opening through which the probe can be inserted from the back and locked in position in the probe holder.

18 Claims, 4 Drawing Sheets

36
35
12
37
III
16
IV
17
VI
20
V
15
41
14
13
II
34
11
I

ROBOT FOR ULTRASONIC EXAMINATION

This application is a continuation-in-part of International Application PCT/SE2004/001492, having an international filing date of Oct. 18, 2004, published in English under PCT Article 21(2).

TECHNICAL FIELD

This invention relates to a robot for medical ultrasonic examination comprising an articulated robot arm with a plurality of arm units successively mounted one on the other to be movable thereon, and a computerised system for controlling the movements of the arm, the outermost arm unit being arranged to carry a probe.

BACKGROUND OF THE INVENTION

Ultrasonic examination is a common method. Usually, the transducer probe is held by hand. It is possible to transmit ultrasonic images over internet to an expert, telemedicine. It is desirable that the expert himself controls the positioning of the probe in real time, which calls for a robot that is convenient to control. Also when the expert is at hand, it is desirable to have such a robot instead of having a hand-held probe.

SUMMARY OF THE INVENTION

It is an object of the invention to permit for a convenient control of the movement of the probe during an examination procedure. It is also an object to make the replacement of the probe simple and fast. According to the invention, the outermost arm unit has a carrying member that is turnable about its longitudinal axis and carries a probe holder that is pivotable on the carrying member about a transverse axis perpendicular to said longitudinal axis. Preferably, the probe holder should include a housing pivotable about said transverse axis and a holder sleeve turnable about its longitudinal axis and said three axes should intersect at a single point. Preferably, the probe holder has an opening through which the probe can be inserted from the back and locked in position transverse to the longitudinal axis of the outermost arm when the probe holder is in a position transverse to the longitudinal axis of the outermost arm. Preferably, the carrying member has a lateral opening through which a cable from the rear of the probe extends. A computerized system is provided for remote control of movements of the arm units about the three axes, the computerized system including motors for effecting the movement for positioning the probe.

DETAILED DESCRIPTION OF THE BEST MODES FOR CARRYING OUT THE INVENTION

Figure 1:
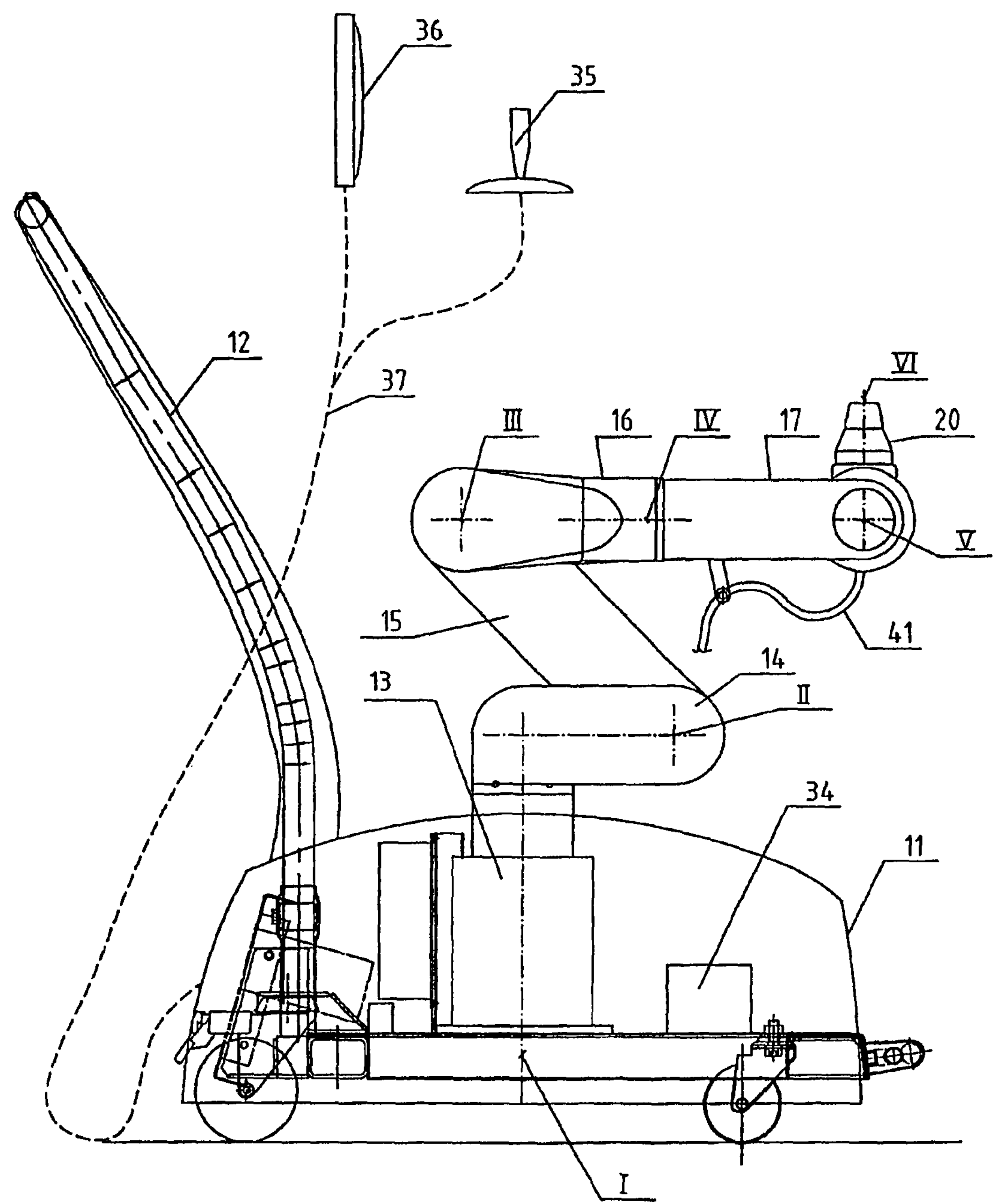
FIG. 1 shows in a side view a robot as an example of the invention.
Figure 2:
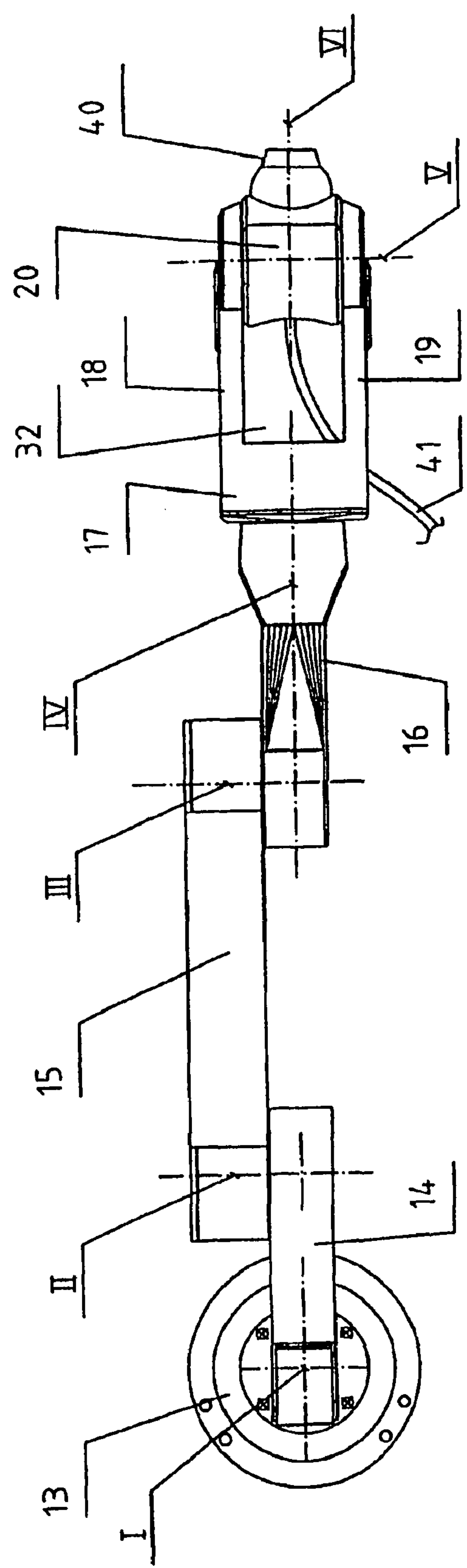
FIG. 2 is a top view of the robot shown in FIG. 1.

As shown in FIG. 1, the robot has base 11 on wheel ant it has a handle 12. The base is shown cut up so that its interior is shown. The wheels can be locked to make the base stand stably. The base has a vertical mount 13 for a first unit 14 of an articulated arm comprising arm units 14-16 and a probe holder 20. The mount 13 and thereby the arm unit 14 is turnable about the vertical axis I and the arm units 15 and 16 are pivotable about the respective axes II and III which are parallel with each other and perpendicular to axis I. The arm unit 16 has an outer portion 17 that is turnable about the longitudinal axis IV of the arm. This portion 17 is bifurcated and between its two extensions 18,19, FIG. 2, it carries the probe holder 20 which is pivotable about a transverse axis V perpendicular to the longitudinal axis IV. The arm 14-16 is not shown in the same position in FIGS. 1 and 2.

Figure 3:
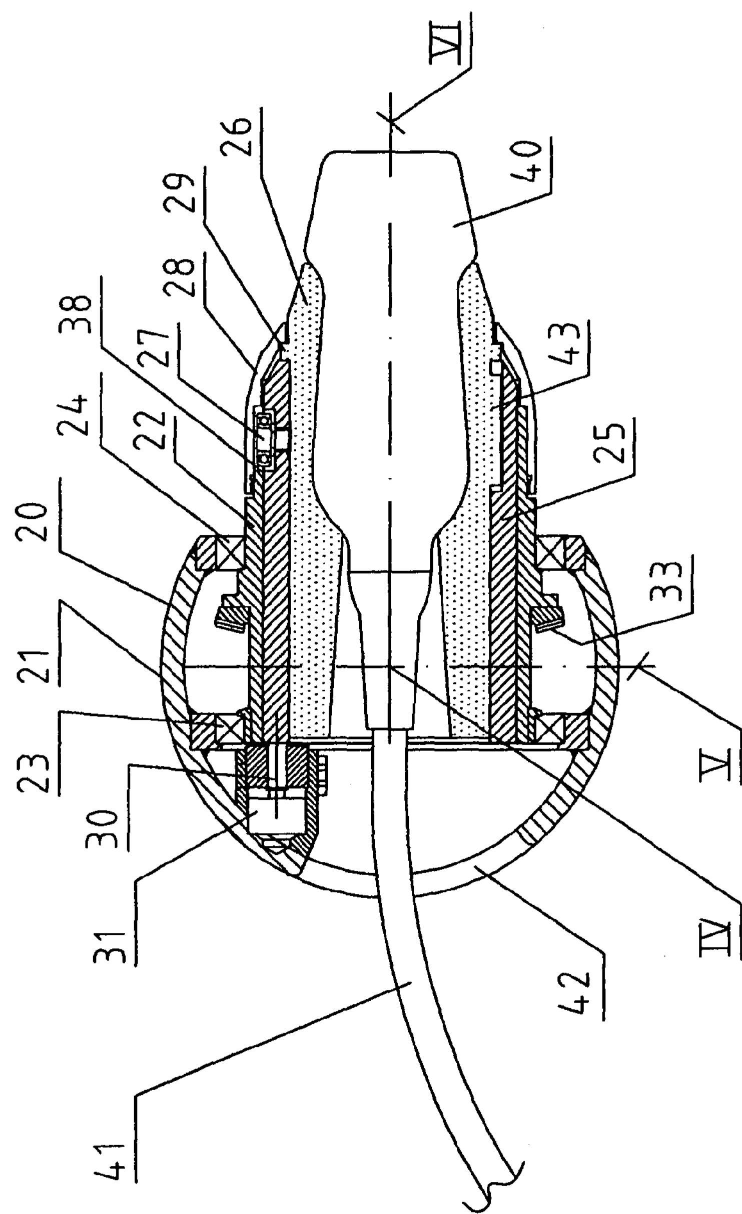
FIG. 3 shows in a longitudinal section and enlarged a detail of the robot.

The probe holder 20 with its probe 40 is shown in FIG. 3 in the same position as FIG. 1, that is with the axis VI transverse to the axis IV. It comprises a housing 21 with a steel tube 22 rotatable in bearings 23,24 in the housing about the axis VI of the probe but axially fixed. Another steel tube 25 inside tube 22 is locked to rotate together with the tube 22 by means of a bearing 27 that is fixed to the tube 25 and slideable in an axial groove 38 in the tube 22 so that the inner tube 25 will be axially slideable a limited length of one or a few mm in the outer tube 22. The bearing 27 ensures that there will be no friction that hinders axial movement of the inner tube 25 if there is a tangential force between the two tubes 22,25. Inside the inner tube 25 is a longitudinally split insert 26 of plastic that is adapted to the form of the probe and holds the probe fixed in it. An annular cap 28 is screwed to the outer tube 22 and engages with an annular shoulder 29 on the insert 26 to prevent the insert from falling out. The inner tube 25 has an axial groove for an axial ridge 43 on the insert 26 so that the insert cannot turn in the inner tube.

When there is an axial force on the probe 40, the shoulder 29 on the insert 26 transmits the axial force to the tube 25 which transmits the force to a pin 30 that exerts the force onto a force sensor 31 that provides an electrical signal via a non-illustrated line to an electronic unit 34 in the base 11.

There are different probes for different ultrasonic medical examinations and the probes are easily interchangeable. For replacing a probe for the one mounted with the probe holder in its position shown in FIGS. 1 and 3, one removes the cap 28, and pushes out the tube 25 forwards. Then, the insert 26 with the probe is pushed out of the tube 25 and the split insert 26 is separated from the probe and the probe is pulled backwardly in its cable 41 out of the tube 22 and out of the housing 21. The opening 42 at the back of the housing 21 and the tube 22 are dimensioned to permit for this withdrawal of the probe. The cable extends sideways out through one of the lateral openings 32 that are provided between the two extensions 18, 19 of the bifurcated portion 17, and the probe can be pulled through the opening 32.

Now another probe can be moved through the outer tube 22 and mounted in the inner tube 25 with inserts adapted for this particular probe. Then, the inner tube 25 with inserts and probe are inserted in the outer tube 22 and the cap 28 is screwed on. The probe is thus moved through the point where the three axes IV, V, and VI intersect and the distance between the axis V and the point of the probe, when the probe is in place, is small. The probes are normally elliptical and, therefore, such probes need not be held against rotation in the inserts solely by friction.

Figure 4:
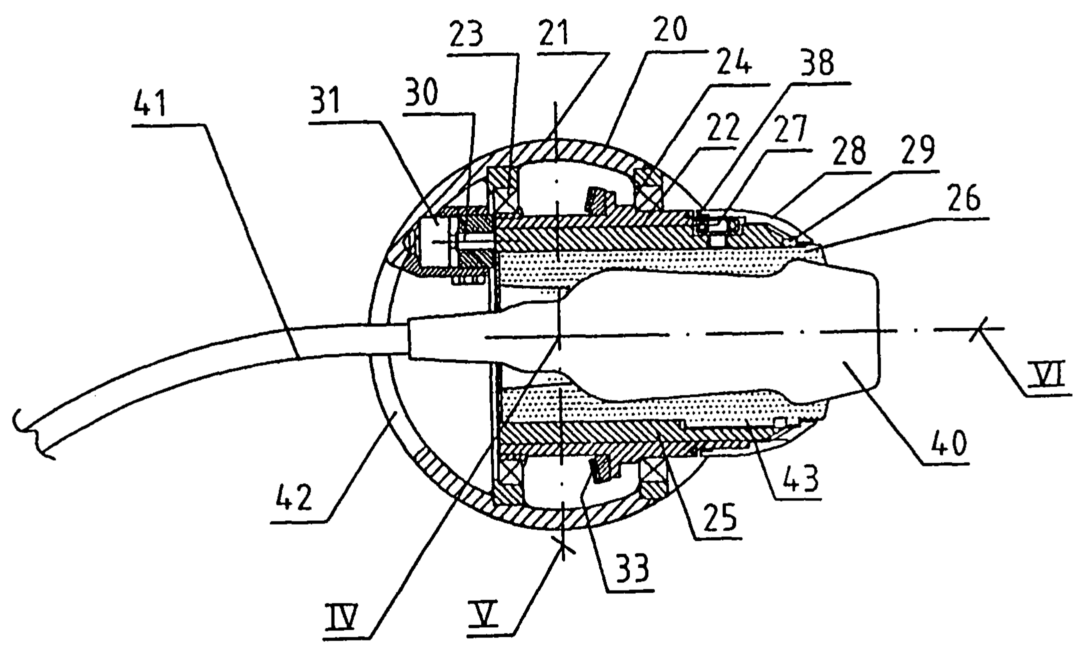
FIG. 4 is similar to FIG. 3, and clearly illustrates the intersection of three axes within the probe.

FIG. 4 is similar to FIG. 3, and the same reference numerals are used to designate the same elements in FIGS. 3 and 4. FIG. 4 clearly discloses that Axes IV, V, and VI intersect at a single point within the probe 40.

The robot includes built-in motors, electric motors, for carrying out the pivoting or rotation about the axes I-VI. The motors and their transmissions are not illustrated. The two motors for pivoting about the axes V and VI are placed inside the portion 17 of arm 16 and they transmit movement via transmission belts, one belt in each extension 18,19. The transmission belt for rotating the outer tube 22 rotates a non-limited gear that engages with a ring gear 33 on the tube. Thus, in order for maintaining the outer tube fixed in the housing 21, the motor for rotating the outer tube must be actuated when the housing 21 is pivoted about the axis IV by the other motor in order to counteract the rotation of the tube 22 that otherwise would occur.

The computerised system for controlling the movements of the arm and prove includes the computerised electronic unit 34 in the base 11 coupled to a control unit for example in the form of a joystick 35 and some buttons or a joystick and a keyboard. The force sensed by the force sensor will appear on a display (monitor) 36. The ultrasonic image from the probe will also appear on the same display or on a separate display. The line between the electronic unit and the operator's panel is indicated with dashed lines 37. The operator, that is, the medical expert can be in the room or he can remote control the robot via internet or other communication means (telemedicine examination).

The computerised system includes two control systems:

The first programmed control system controls the probe in cartesian coordinates which means that the probe is moved in X, Y and Z coordinates in response to movement of the joystick, that is the joystick controls the movements about all the axes and the direction of the probe is maintained constant during its movement.

The second programmed control system controls the probe in an Euler angle system, which means that the direction of the probe is controlled by the joystick but the point of the probe is not moving sideways.

In both control systems, the medical expert need not control the individual movements about the axes I-VI but he simply uses the joystick to move the probe.

The programming is not described since it can be carried out in various ways by any skilled programmer.

Description of the Operation of the Illustrated Robot in a Telemedicine Examination Step 1:

The assistant on site helps the patient to right position for the examination and moves the robot to position and locks the wheels of the robot. The medical expert may have real time video contact so that he/she can instruct the assistant.

Step 2:

The medical expert remote controls the robot and chooses the pre-programmed start position suitable for the examination to be carried out.

Step 3:

The expert chooses the cartesian control system and moves the robot arm by means of the joystick and chooses a suitable force applied by the probe to the patient. When the point of the probe is at the right place, the expert switches to the Euler angle control system and adjusts the direction of the probe with the probe point not moving sideways. The expert may also alternate between the two control systems several times for carrying out an examination in order to get the best possible positioning and to get the desired images. The distance between the axis V and the point of the probe is small, which facilitates its positioning. He may also switch to another pre-programmed start position and start over again with the probe at another position on the patient.

The invention claimed is:

1. A robot for medical ultrasonic examination comprising:

an articulated robot arm comprising a plurality of arm units (14-16) successively mounted one on the other to be pivotable one on the other, a carrying member (17, 18, 19) mounted on the outermost one of the arm units (16) so as to be rotatable about the longitudinal axis (IV) thereof, and a probe holder (20) mounted on the carrying member so as to be pivotable about an axis (V) perpendicular to said longitudinal axis (IV) and comprising a holder sleeve (25) rotatable about an axis (VI), said holder sleeve being arranged to carry a probe coaxially therein, and a computerised system (34) for remote control of the movements of the arm units and for movements about said three axes (IV, V, VI), said three axes intersecting at a single point, the computerised system including motors for effecting the movements for positioning the probe, the probe holder (20) having an opening through which the probe (40) can be inserted from the back and be locked in position in the probe holder when the probe holder is in a position transverse to the longitudinal axis (IV) of the outermost arm.

2. A robot according to claim 1, wherein said carrying member (17, 18, 19) has a lateral opening (32) through which a cable (41) from the rear end of the probe (40) extends when the probe is mounted.

3. A robot according to claim 2, wherein a force sensor (31) in the probe holder (20) is arranged to sense the axial force on the probe (40).

4. A robot according to claim 2, wherein the holder sleeve (25) comprises a replaceable insert (26) adapted to the form of the actual probe (40) in use.

5. A robot according to claim 2, wherein the probe holder is arranged such that the intersection of the three axes (IV, V, VI) lies within the probe when the probe (40) is mounted in the probe holder (20).

6. A robot according to claim 1, wherein said carrying member (17, 18, 19) has a bifurcated portion in which the probe holder (20) is pivotably mounted for permitting a cable of the probe to extend sideways out between the two extensions of the bifurcated portion.

7. A robot according to claim 6, wherein a force sensor (31) in the probe holder (20) is arranged to sense the axial force on the probe (40).

8. A robot according to claim 6, wherein the holder sleeve (25) comprises a replaceable insert (26) adapted to the form of the actual probe (40) in use.

9. A robot according to claim 6, wherein the probe holder is arranged such that the intersection of the three axes (IV, V, VI) lies within the probe when the probe (40) is mounted in the probe holder (20).

10. A robot according to claim 1, wherein a force sensor (31) in the probe holder (20) is arranged to sense the axial force on the probe (40).

11. A robot according to claim 10, wherein the computerised system (34) is arranged to permit for an adjustment of the maximum allowed force to be sensed by the force sensor (31) when the probe (40) is in contact with a patient.

12. A robot according to claim 10, wherein the holder sleeve (25) comprises a replaceable insert (26) adapted to the form of the actual probe (40) in use.

13. A robot according to claim 10, wherein the probe holder is arranged such that the intersection of the three axes (IV, V, VI) lies within the probe when the probe (40) is mounted in the probe holder (20).

14. A robot according to claim 1, wherein the probe holder comprises a housing (21), in which the holder sleeve is limitedly axially movable, and a force sensor (31) is coupled between the holder sleeve and the housing.

15. A robot according to claim 14, wherein the computerised system (34) is arranged to permit for an adjustment of the maximum allowed force to be sensed by the force sensor (31) when the probe (40) is in contact with a patient.

16. A robot according to claim 1, wherein the holder sleeve (25) comprises a replaceable insert (26) adapted to the form of the actual probe (40) in use.

17. A robot according to claim 16, wherein the replaceable insert (26) is longitudinally split.

18. A robot according to claim 1, wherein the probe holder is arranged such that the intersection of the three axes (IV, V, VI) lies within the probe when the probe (40) is mounted in the probe holder (20).

* * * * *